United States Patent [19]

Pless et al.

[11] Patent Number: 4,952,864
[45] Date of Patent: Aug. 28, 1990

[54] POWER SUPPLY DOWN-CONVERSION, REGULATION AND LOW BATTERY DETECTION SYSTEM

[75] Inventors: Benjamin Pless, Menlo Park; John G. Ryan, San Jose, both of Calif.

[73] Assignee: Ventritex, Sunnyvale, Calif.

[21] Appl. No.: 360,007

[22] Filed: Jun. 1, 1989

Related U.S. Application Data

[62] Division of Ser. No. 259,382, Oct. 18, 1988, Pat. No. 4,868,908.

[51] Int. Cl.⁵ ............................................. G05F 5/00
[52] U.S. Cl. ..................................... 323/299; 340/663; 340/636
[58] Field of Search ............... 323/267, 271, 293, 299, 323/352, 364; 363/62; 320/1; 307/109, 110; 340/636, 660–663

[56] References Cited

U.S. PATENT DOCUMENTS

| | | | |
|---|---|---|---|
| 2,944,198 | 7/1960 | Louys | 323/364 |
| 3,036,263 | 5/1962 | Hallas | 323/364 |
| 4,205,369 | 5/1980 | Asano | 363/62 |
| 4,404,624 | 9/1983 | Yamazaki | 363/62 |
| 4,451,743 | 5/1984 | Suzuki et al. | 320/1 |
| 4,460,953 | 7/1984 | Fukushima et al. | 363/62 |

Primary Examiner—Peter S. Wong
Attorney, Agent, or Firm—Limbach, Limbach & Sutton

[57] ABSTRACT

A low battery detect circuit shuts down high current circuitry in the system in the event that battery voltage drops to a level such that the regulated output voltage is endangered. The trigger voltage is dependent upon capacitor ratios and a reference voltage. The output of the detection circuitry is a digital signal which can be used to disable high current circuitry in an implantable medical device and, thus, allow the battery voltage to recover. Alternatively, the output of the detection circuitry can be used as a battery status indicator flag.

6 Claims, 4 Drawing Sheets

POWER SUPPLY DOWN-CONVERSION, REGULATION AND LOW BATTERY DETECTION SYSTEM

BACKGROUND OF THE INVENTION

The most important feature of any battery powered system after the obvious functionality is longevity. The limiting component in the life of such systems is almost invariably the battery amp hour rating. Therefore, particularly in implantible medical devices, power conservation measures are extremely important.

It is well known that the power consumption of a digital system is a function of approximately the square of the power supply voltage. Thus, for example, halving the voltage can potentially result in a fourfold increase in battery longevity.

Another important reason for lower voltage operation in implantible devices is a function of recent trends in integrated circuit technologies, namely, reduction in IC line width generally requires a lower power supply. However, it is typical of implantible devices to incorporate a mix of integrated circuit types with different power supply requirements. For example, power DMOS or VMOS devices typically require in excess of 5V for good operation, while many microprocessor integrated circuits typically require operating voltages in the 3V range. In the particular implantible device application for which the circuitry of the present invention was developed, two operating voltages are required: a battery terminal voltage Vbatt which varies, depending on battery condition, from 4.5V to 6.5V and a regulated 3V supply from which most of the device's digital logic operates.

It will be obvious to those familiar with battery powered devices which include some high power components that it is desirable to monitor battery terminal voltage under high current load. This is due to the fact that excessive dips in battery terminal voltage may endanger the logical states of the circuitry controlling the high power components. Also, excessive terminal voltage dips may be indicative of an impending battery failure which, in the case of an implantible medical device, triggers immediate replacement of the device.

U.S. Pat. No. 4,599,523 issued to Pless et al on July 8, 1986, discloses a power distribution controller that regulates the load placed on a pacemaker power source. The controller selectively sWitches the power source between the output capacitor of the pacemaker's output circuitry and the pacemaker's voltage sensitive control circuitry so that the peak power requirement of the output capacitor does not affect the supply voltage of the control circuit. The control circuit is disconnected from the battery whenever the battery is connected across the output capacitor. When the output capacitor is charging, a hold-up capacitor maintains the control circuit supply voltage at or above the minimum required for powering the control circuit. As required, the controller switches to connect the battery to the control circuit and to disconnect the output circuitry.

SUMMARY OF THE INVENTION

The present invention provides circuitry for detecting when the battery terminal voltage Vbatt drops below a predetermined trigger voltage Vtrig. This trigger voltage Vtrig is dependent only upon capacitor ratios and a reference voltage Vref. The output of the detection circuitry is a digital signal which can be used to disable the high current circuitry in the implantible device and, thus, allow the battery terminal voltage Vbatt to recover. Alternatively, the output of the detection circuitry can simply be used as a battery status indicator flag.

Other features and advantages of the present invention will be understood and appreciated by reference to the detailed description of the invention provided below which should be considered in conjunction with the accompanying drawings.

DETAILED DESCRIPTION OF THE INVENTION

The control circuit of the present invention can be thought of as being composed of several subsystems for efficiently supplying battery current at a regulated voltage which is less than battery terminal voltage and for protecting the regulated voltage from excessive battery voltage dips caused by large currents being drawn directly from the battery terminals. The following description of the operation of such a control circuit in accordance with the present invention is set forth in terms of an illustrative embodiment. However, it should be understood that this is done for purposes of clarity only and should not be interpreted as limiting the applicability of the invention to other circuits.

Figure 1:
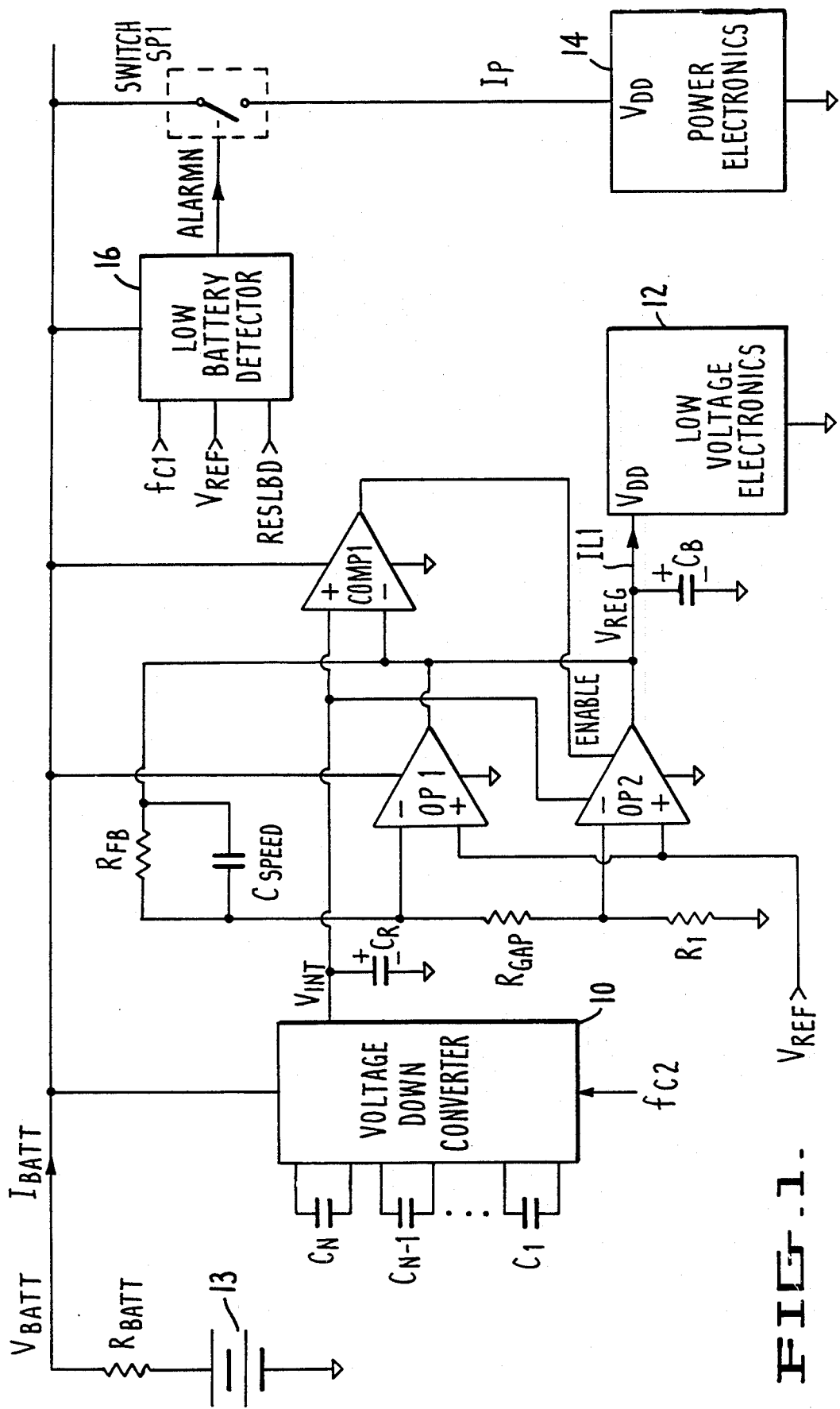
FIG. 1 is a block diagram illustrating control circuitry in accordance with the present invention.

FIG. 1 shows a block diagram of a power supply/low battery detection system in accordance with the present invention. A voltage downconverter 10 is shown in FIG. 1 as configured with N capacitors. This configuration represents the general case in which the output of downconverter 10, a selected intermediate voltage Vint, can be any voltage tap comprising an integer multiple of the battery terminal voltage Vbatt divided by N, up to and including Vbatt. An illustrative example of voltage downconverter 10 is described in greater detail below.

FIG. 1 further shows voltage regulator circuitry comprising operational amplifiers OP1 and OP2, comparator COMP1, resistors $R_{FB}$, $R_{GAP}$, and $R_1$, and capacitors $C_R$, $C_B$ and $C_{SPEED}$. The voltage regulator circuitry generates a regulated voltage Vreg which serves as the supply for low voltage electonics 12.

Low voltage electronics circuit 12 represents a group of circuits that are powered from the regulated voltage Vreg. These circuits might include, for example, a microprocessor and its associated logic devices.

Power electronics block 14 represents circuitry which at certain times can draw substantial current from battery 13. The size of this current may be such that its product with the battery source impedance Rbatt may be a significant portion of the battery potential. Thus, low battery detect circuitry 16 detects when the battery voltage Vbatt dips below a predetermined trigger voltage Vtrig and, in response, disables the power electronics 14 so that the large current draw Ip from the battery 13 is interrupted. This current interruption is illustrated conceptually in FIG. 1 by switch SP1.

Figure 2:
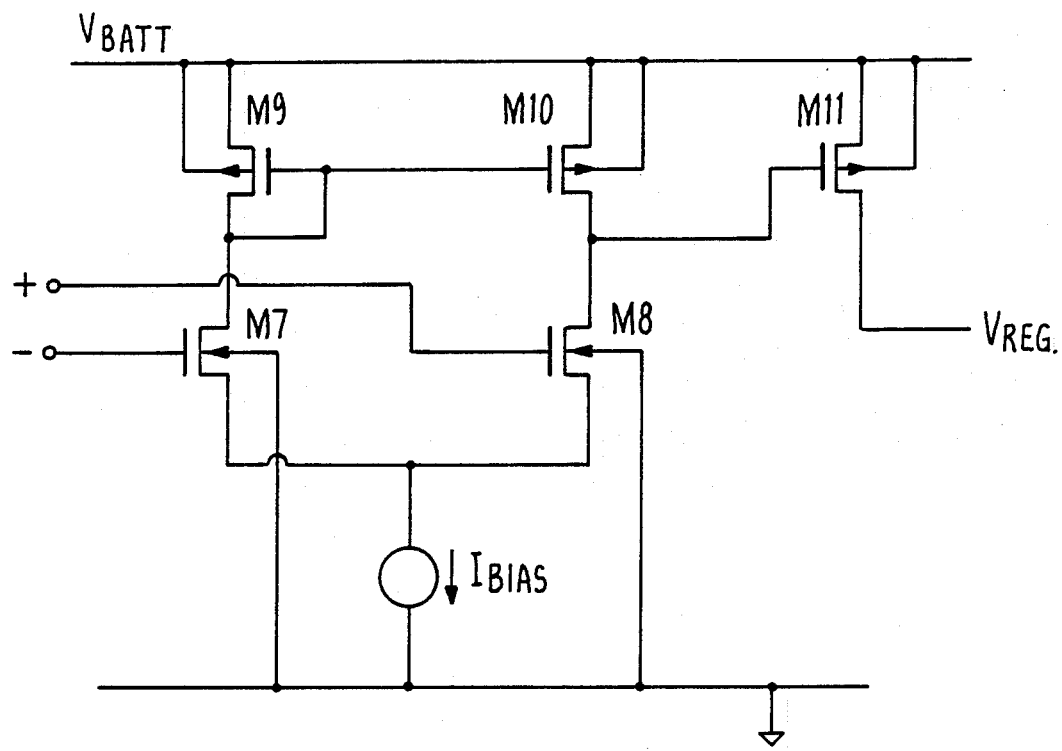
FIG. 2 is a schematic diagram illustrating a circuit embodiment of operational amplifier OP1 in FIG. 1.
Figure 3:
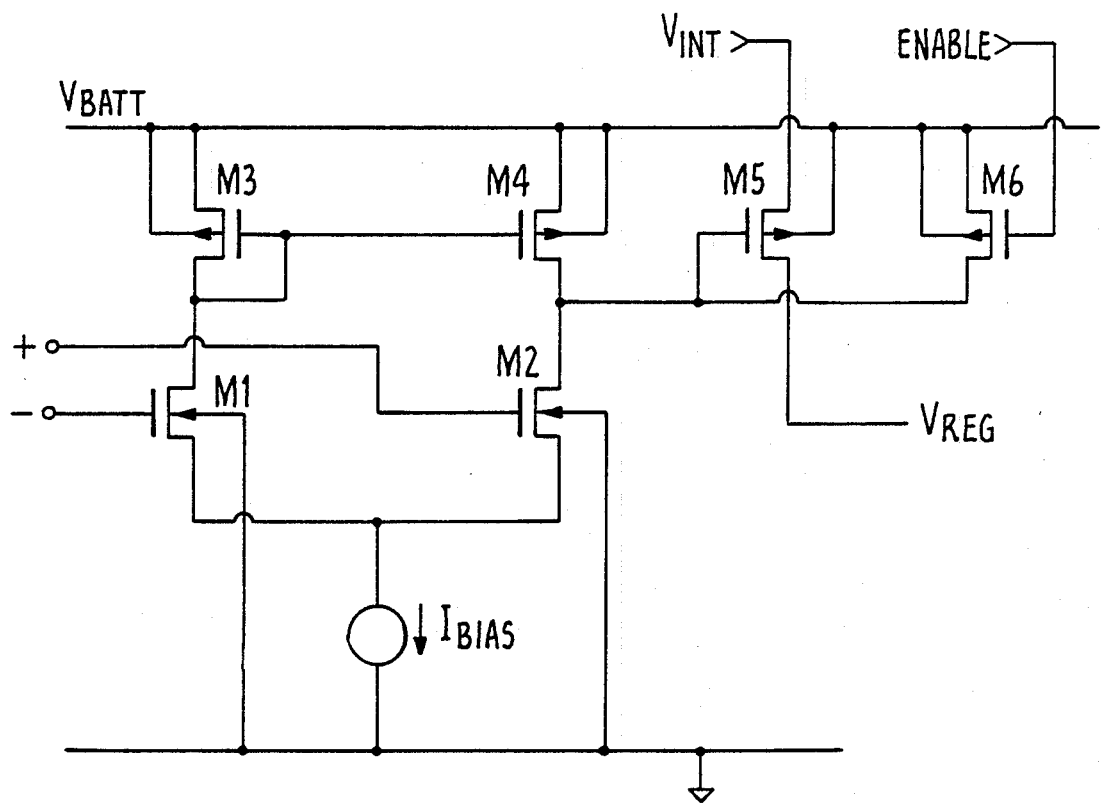
FIG. 3 is a schematic diagram illustrating a circuit embodiment of operational amplifier OP2 in FIG. 1.

FIGS. 2 and 3 show illustrative embodiments of operational amplifiers OP1 and OP2, respectively. Operational amplifier OP1, as shown in FIG. 2, applies a high voltage gain to the differential signal applied between its + and − inputs. The + and − inputs to op amp OP1 are applied to the gates of N-channel amplifier devices M8 and M7, respectively. Devices M8 and M7 are commonly tied to the negative rail via a constant current source $I_{BIAS}$ and are tied to the positive rail, i.e. battery terminal voltage Vbatt, via a current mirror comprising P-channel devices M9 and M10. The output of the differential gain stage of op amp OP1 is provided to the gate of P-channel output device M11 which provides the regulated voltage Vreg.

A comparison of FIGS. 2 and 3 will show that amplifiers OP1 and OP2 are identical except that the P-channel output device M5 of op amp OP2 may be disabled by switching on P-channel device M6 by setting the ENABLE line low. Also, the drain of device M5 is connected to the intermediate voltage Vint.

It is assumed that a substantial percentage of the average device current is expended in the low voltage electronics 12 which is powered from the regulated voltage Vreg. This current is labeled IL1 in FIG. 1.

The total battery power consumed is given by:

$$P = Vbatt * Ibatt$$

where, as shown in FIG. 1, Ibatt is the total current drawn from the battery terminals.

If the battery voltage Vbatt was simply linearly regulated down to the regulated voltage Vreg level, a substantial percentage of the battery power output would be dissipated in the regulator. This power loss is given by:

$$Plossreg = IL1 * (Vbatt - Vreg) \quad (1)$$

It is clear that power loss is a function of the difference between the battery voltage Vbatt and the regulated voltage Vreg. Thus, an efficient voltage downconverter to an intermediate voltage Vint between Vreg and Vbatt would improVe overall efficiency.

Efficiency without the voltage downconversion, efined as power used divided by power drawn from the battery, is given by:

$$e = Vreg/Vbatt \quad (2)$$

Thus, with Vreg=3V and Vbatt=6V, the efficiency is 50% at best. With a downconverter working with efficiency y, the efficiency becomes:

$$e = y * Vreg/Vint,$$

where intermediate voltage Vint is the output of the downconverter.

Thus, with Vint=2/3 (Vbatt) and Vbatt=6V as before, and assuming a lossless downconversion, the maximum efficiency becomes:

$$E = 3/2 * e \text{ or } 75\% \text{ in this case.} \quad (3)$$

This means that for every 3I supplied by regulated voltage Vreg, only 2I is drawn from battery terminal voltage Vbatt, thus potentially allowing for up to a 33% increase in battery longevity, assuming negligible current on average being drawn directly from the battery 13.

The above analysis assumes that Vint=Vbatt * 2/3; but other possibilities exist for intermediate voltage Vint. In the general case of an N capacitor downconverter, for example, any integral multiple of Vbatt/N can be chosen for Vint or, indeed, a number of voltage outputs might be selected in sequence as battery voltage Vbatt drops throughout life to end of service.

As an example, consider N=4 with Vreg=3V and Vbatt starting at 6.5V and reaching end of service at 5V. Initially, the Vbatt/2 output would be selected as the intermediate voltage Vint, which would be sufficient to support regulated voltage Vreg until battery voltage Vbatt dropped close to 6V. With Vbatt below 6V, the Vbatt * 3/4 output would be selected as Vint, which could support Vreg to end of service. For the initial part of battery life, i.e. from 6.5V to 6V, the efficiency would approach $$E = 2 * Vreg/Vbatt = 96\% \text{ at } Vbatt = 6.25V \quad (4)$$

while for Vbatt between 6V and 5V, the efficiency would approach $$E = 4/3 * Vreg/Vbatt = 73\% \text{ at } Vbatt = 5.5V \quad (5)$$

Figure 4:
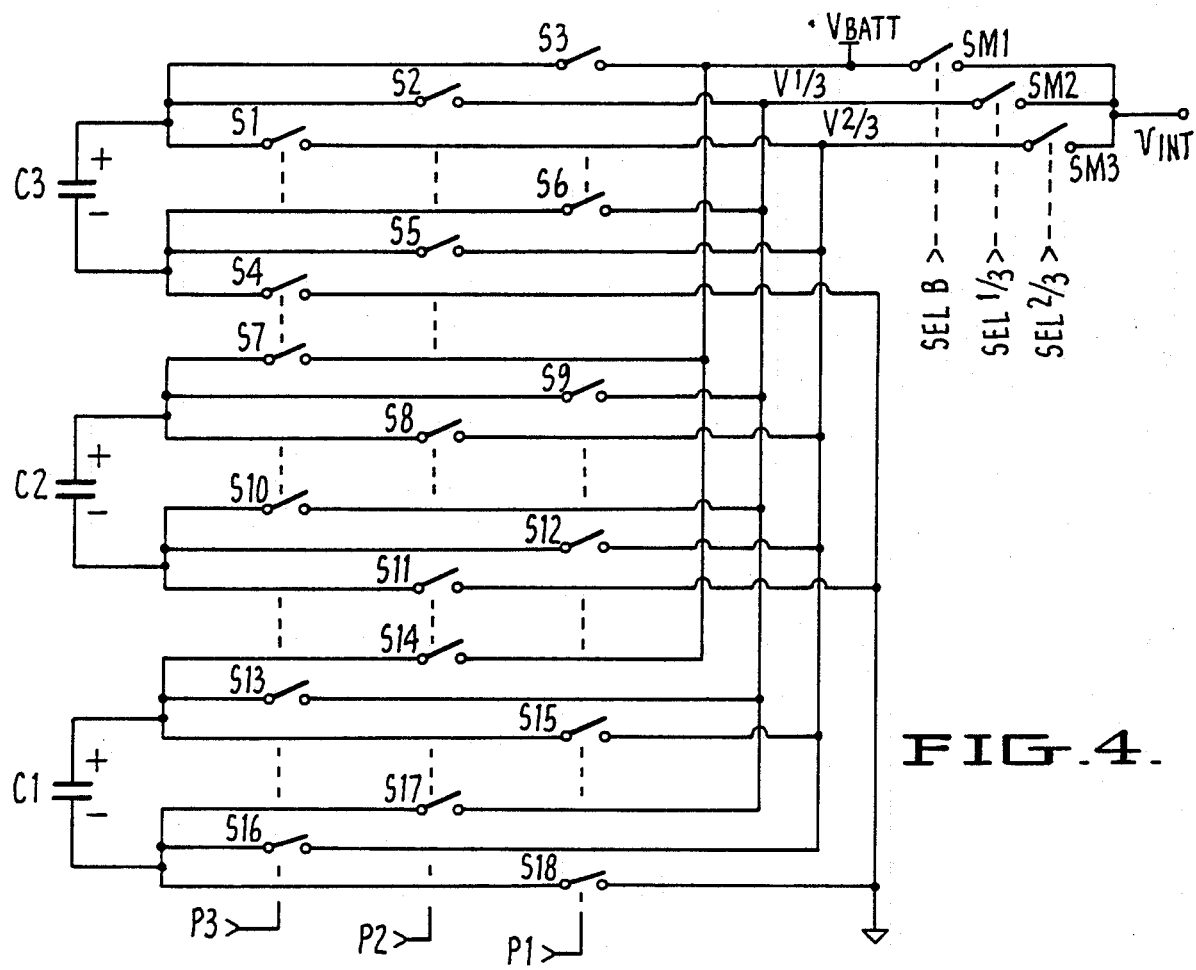
FIG. 4 is a schematic diagram illustrating a circuit embodiment of a voltage downconverter in accordance with the present invention.

FIG. 4 shows the arrangement of switches and capacitors for a voltage downconverter 10 with N=3. Two downconverted voltage taps are available, i.e. 1/3 (Vbatt) and 2/3 (Vbatt), shown in FIG. 4 as V1/3 and V2/3, respectively. Switches S1 through S18 and switches SM1 through SM3 are shown as relays for clarity, but in practice are preferably electronic switches which can pull to both power rails. It will be clear to those skilled in the art that these switches could be CMOS transmission gates.

Switches SM1 through SM3 comprise a multiplexor that allows for the selection of one of Vbatt, V1/3(Vbatt) or V2/3(Vbatt) as Vint by asserting one of the control lines SELB, SEL1/3 or SEL2/3, respectively.

Figure 5:
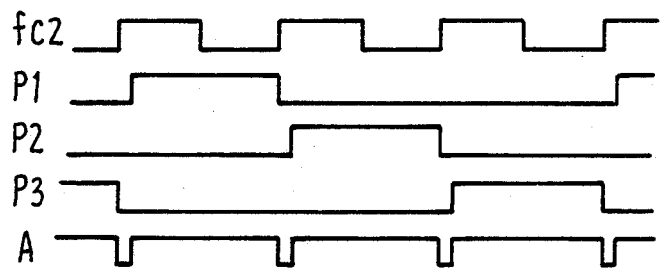
FIG. 5 is a timing diagram illustrating the timing relationships of the P1, P2 and P3 clock phases utilized in the FIG. 4 voltage downconverter in relation to master clock fc2.
Figure 6:
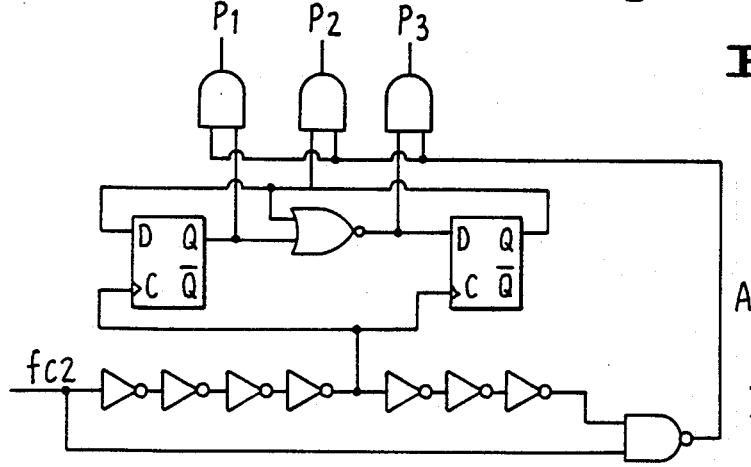
FIG. 6 is a logic diagram illustrating an embodiment of circuitry which can be used to generate the P1, P2 and P3 clocks.

Switches S1 through S18 are driven by clock phases P1, P2 and P3. The switching phases for clocks $P_1$, $P_2$ and $P_3$ are shown in FIG. 5. FIG. 6 provides a logic diagram that illustrates the derivation of the P1, P2 and P3 clocks from a master clock fc2.

Referring back to FIG. 4, the illustrated downconverter circuit 10 consists of 3 equal-valued capacitors C1, C2 and C3 and 18 switches which, as mentioned above, can be implemented with CMOS transmission gates. The Ron of the switches is chosen to be small in relation to the switched capacitor impedance of the circuit.

As can be deduced from of FIGS. 4 and 5, operation of downconverter circuit 10 consists of connecting the three capacitors C1, C2 and C3 in series between the battery voltage Vbatt and ground in different orders during each of the three clock phases P1, P2 and P3. For example capacitor C3 is connected between battery voltage Vbatt and V2/3 during P1, between V2/3 and V1/3 during P2 and between V1/3 and ground during P3. Capacitors C2 and C1 follow this pattern except that they are two and one full cycles of master clock fc2 out of phase, respectively.

The downconverter circuit 10, thus, functions as a switched capacitor voltage divider while the V2/3 output approaches Vbatt * 2/3 and the V1/3 output approaches Vbatt * 1/3, assuming negligible loading.

The component of output impedance due to the switched capacitor action can be deduced from looking at the source capacitance at the V2/3 output. The current loading causes a voltage drop during each active clock phase given by:

$$dV = I\ load/(fc2 * C\ source) \quad (6)$$

This drop appears as ripple on the V2/3 output and is filtered by the capacitor $C_R$ in FIG. 1.

Assuming that the output impedance can be approximated by:

$$\begin{aligned}&Rsc = \text{Average } dV/Iload, \text{ then;}\\&Rsc = 1/(3 * C * fc2), \text{ where } C \text{ is}\\&\text{the value of each capacitor } C_1, C_2\\&\text{and } C_3.\end{aligned} \quad (7)$$

For example with C=100 nF and fc2=4 kHZ, then Rsc=0.83 kohm.

With regard to the contribution of the switch resistances Ron, a worst case analysis in the N=3 case described above would take the equivalent resistance of the switch combination with each capacitor shorted:

$$Rsw = 2 * Ron \text{ in parallel with } 6 * Ron = 1.33 * Ron \quad (8)$$

(An additional Ron should be included if the multiplexor arrangement comprising switches SM1 through SM3 is considered.)

Reference is made above to "y", which related to the efficiency of the downconversion circuit. The value of y can be estimated as follows for N=3 with Vint=V2/3

$$\begin{aligned}y &= \text{power out/power in}\\&= 1 - Ploss/Pin\\&= 1 - (3 * IL1 * Rout/2 * Vbatt)\end{aligned}$$

where Rout is the total output impedance of the downconverter.

IL1 is the current drawn from downconverter 10.

For example, with IL1=20 microamps, Rout=1 kohm and Vbatt=6 V, the efficiency y approaches 99.5%. The value of y will, in fact, be lower when the overhead of operating the control logic at frequency fc2 is considered.

Referring back to FIG. 1, amplifiers OP1 and OP2 are configured in parallel with non-inverting gains of:

$$[1 + R_{FB}/(R_{GAP} + R_1)] \text{ for } OP1$$
$$\text{and } [1 + (R_{FB} + R_{GAP})/R_1] \text{ for } OP2$$

Assuming $R_{GAP}$ is small compared with $R_1$ and $R_{FB}$, amplifier OP2 attempts to regulate to a voltage Vregh slightly higher than that of amplifier OP1. Conflict between these two amplifiers is removed by judicious choice of an amplifier structure which, as stated above, does not include an active pull down device on the output node. The actual regulation voltages are the product of the reference voltage Vref and the individual amplifier gains. Amplifier OP2 will dominate if its power supply, intermediate voltage Vint, is greater than the output voltage Vreg. In this case, amplifier OP1 will be biased off and, hence, all the output current will be drawn through the voltage downconverter 10.

In the case where intermediate voltage Vint drops below Vreg, Vreg will drop such that amplifier OP1 will source current directly from the battery and will regulate at a slightly lower voltage than before. This voltage is denoted Vregl.

Thus, Vregh and Vregl are the high and low limits, respectively, on the Vreg line.

Referring to FIG. 1, capacitor $C_{SPEED}$, which is connected across the $R_{FB}$ resistor, has the effect of speeding up the response of the regulator circuitry to a switched load. A typical value of capacitor $C_{SPEED}$ is 47 nF.

As shown in FIGS. 1 and 3, voltage comparator COMP1 disables the output transistor M5 of amplifier OP2 when intermediate voltage Vint drops below Vreg. This is necessary to prevent battery current from being sourced through transistor M11 of amplifier OP1 and, hence, through transistor M5 into Vint. If this were allowed to occur, intermediate voltage Vint would be pumped to a voltage higher than its proper operating point, causing a reduction in efficiency and increasing the ripple component of the battery voltage.

The size of the voltage difference between Vregh and Vregl, denoted Vdiff, is given by:

$$Vdiff = Vref \\ [R_{FB}/(R_{GAP}+R_1) - R_{FB}/R_1 - R_{GAP}/R_1] \quad (9)$$

Note that for fixed $R_{FB}$ and $R_1$, Vdiff can be adjusted by the value of $R_{GAP}$. For example, given:

Vref=1.235V (Silicon Bandgap)

$R_{FB}$=4 Mohm $R_1$=3 Mohm $R_{GAP}$=100K ohm gives Vdiff=95 mV with Vregh=2.92V and $R_{GAP}$=200K ohm gives Vdiff=186 mV with Vregh=2.96V.

It is desirable to keep Vdiff as small as possible so as to confine the range over which Vreg varies with battery voltage. The limit to how small Vdiff can be set is determined by the worst case amplifier voltage offsets that can be expected. If both amplifiers have equal but opposite maximum offset Vosmax then, $$V_{diff}\ GT\ 2 * V_{os}\text{max} * (\text{max loop gain})$$
i.e., $V_{diff}\ GT\ 2 * V_{OS}\text{max} * [1 + (R_{FB} + R_{GAP})/R_1]$ Hence, in the above example with Vdiff=95 mV, Vosmax would be 20 mV, which is a reasonable value for good quality CMOS operational amplifiers.

As stated above, op amps OP1 and OP2 are CMOS amplifiers without an active pull down N-channel device on their outputs. It is assumed that the gain setting resistors $R_1$, $R_{GAP}$ and $R_{FB}$ and the load current IL1 are sufficient to counteract leakage through the output P-channel devices M5 and M11. As stated above, the output of op amp OP2 can be made high impedance (i.e. disabled) using the ENABLE control line.

Frequency compensation is achieved by the addition of capacitor $C_B$ between Vreg and ground. The combination of the amplifier output impedance and capacitor $C_B$ form a dominant pole in the amplifier frequency response. Capacitor $C_B$ also serves as a decoupling capacitance for low voltage electronics 12.

As mentioned above, the combination of a large digital system operating from a regulated supply and a high current circuit drawing current directly from the battery, albeit infrequently, suggests the need for a circuit to both detect a low battery and prevent a reset of the digital system by disabling the high current circuitry. This is important in implantible medical electronics, particularly in a defibrillator, since the digital systems contain physician presets which would be lost by even a momentary loss of power.

Figure 7:
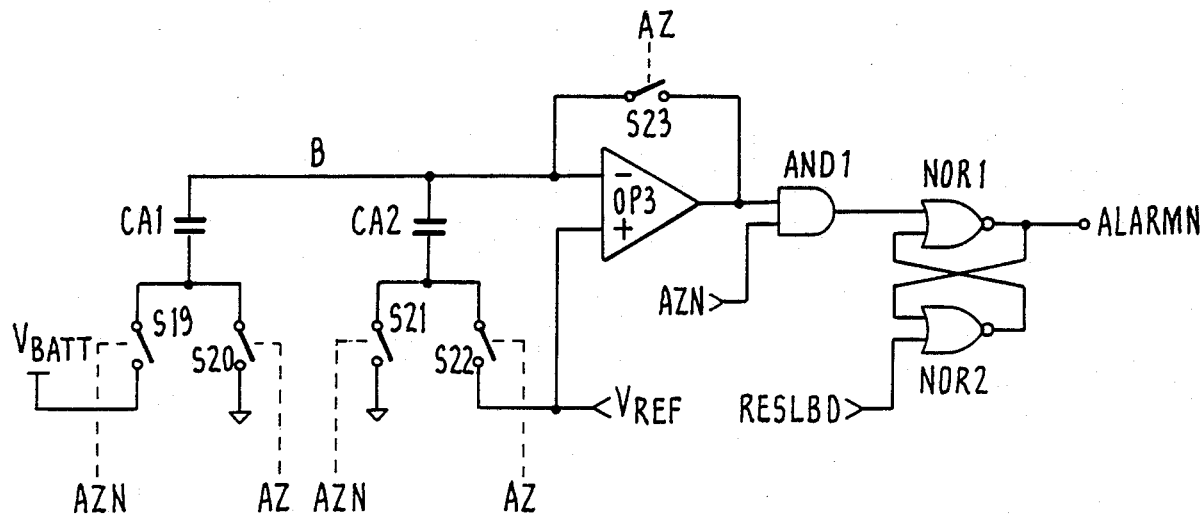
FIG. 7 is a schematic diagram illustrating an embodiment of a low battery detector circuit in accordance with the present invention.

FIG. 7 shows low battery detector circuitry in accordance with the present invention. It consists of two precisely ratioed capacitors CA1 and CA2, an operational amplifier OP3, switches S19-S23, AND gate AND1 and a cross-coupled latch comprising NOR gates NOR1 and NOR2. The control lines for the detector circuitry are AZ (Autozero), AZN (Not Autozero) and a reset RESLBD. The output ALARMN goes low when battery voltage Vbatt drops below a preselected trigger voltage Vtrig.

Figure 8:
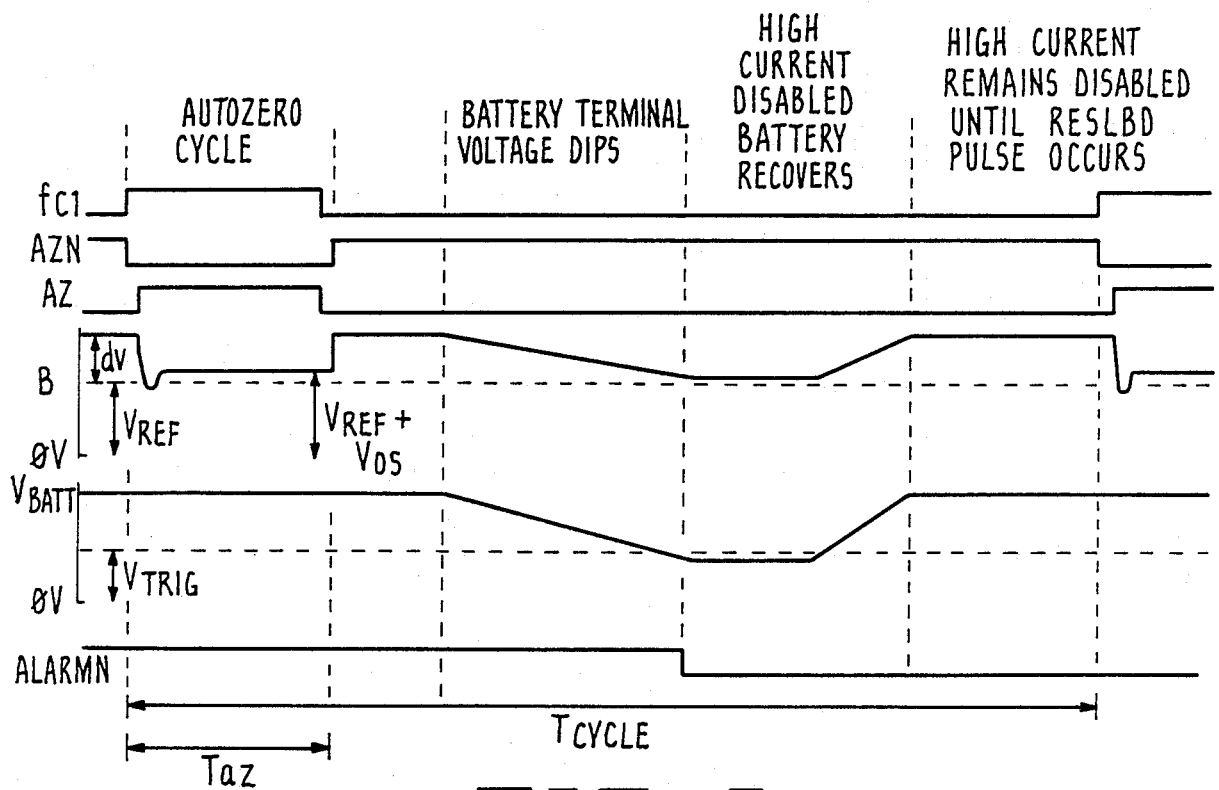
FIG. 8 is a timing diagram illustrating a typical timing waveform for a low battery detection cycle of the circuit shown in FIG. 6.

Referring to FIGS. 7 and 8, during the autozero cycle, operational amplifier OP3 is configured in unity gain and, hence, its inverting input, which is also the top plate of capacitors CA1 and CA2 (node B), is charged to Vref+Vos, where Vos is the amplifier offset voltage. During this time, the bottom plates of capacitors CA1 and CA2 are charged to ground and Vref, respectively. At the end of the autozero cycle, all switches S19-S22 are opened and op amp OP3 acts as a comparator.

On the leading edge of AZN, which is non-overlapping with AZ, the bottom plates of capacitors CA1 and CA2 are switched to battery voltage Vbatt and ground, respectively. The charge on the top plate of capacitors CA1 and CA2 is, thus, changed by a dQ given by:

$$dQ = V_{batt} * CA2 - V_{ref} * CA1 \tag{10}$$

If the battery voltage Vbatt is greater than (CA1/CA2) * Vref, then dQ will be positive, resulting in an increase in voltage dV at node B which in turn drives the output of op amp OP3 negative. Assuming that the Set/Reset latch comprising NOR gates NOR1 and NOR2 has previously been set such that ALARMN is high, the low going output of op amp OP3 will leave the latch in an unchanged state.

If, on the other hand, the battery voltage Vbatt is less than (CA1/CA2) * Vref, then a negative dV results, causing the output of op amp OP3 to switch high, thus resetting the latch and flagging a low battery. The trigger level for this to occur is thus:

$$V_{trig} = (CA1/CA2) * V_{ref} \tag{11}$$

A number of factors should be noted. First, this low battery detect circuit is insensitive to parasitic capacitance on node B, assuming that op amp OP3 has a high gain. Second, the trigger level Vtrig is independent of the amplifier offset voltage Vos, since this is cancelled during the autozero operation. Third, the trigger level Vtrig can be very precisely defined on an integrated circuit since it relies only on a capacitor ratio and a reference voltage. It is well known to those skilled in the art that capacitor ratioing in integrated circuits can be controlled to about 0.1% accuracy. For example, reference may be made to "Analog MOS Intgrated Circuits for Signal Processing" by Gregorian and Temes (Wiley), Chapter 3, for details on achieving such ratioed accuracy. Fourth, the exact configuration of the digital logic is dependent on the application and is described herein as an illustrative embodiment. This particular embodiment relies on reference voltage Vref being less than the trigger level of AND gate AND1 to avoid spurious high going glitches on its output and, hence, erroneously resetting the latch. Delaying the signal to the second input of AND gate AND1 to allow for op amp OP3 settling would remove the glitches in the event of reference voltage Vref being higher.

Figure 9:
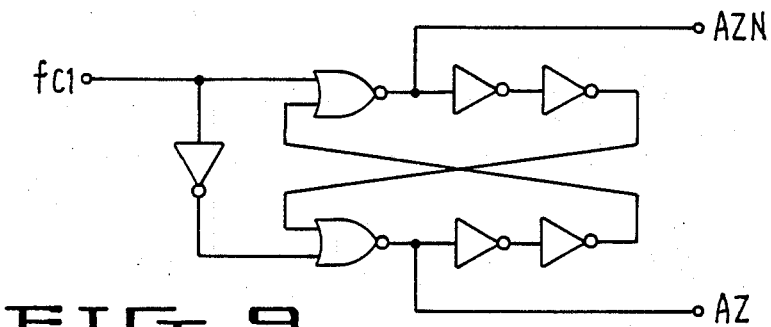
FIG. 9 is a logic diagram illustrating an embodiment of circuitry which can be used to generate the control signals Autozero AZ and Not Autozero AZN utilized in the FIG. 7 low battery detector circuit.

The duty cycle of clock fc1, which controls the autozero cycle, is assumed to be small. This is necessary since, during autozero time, the circuit cannot detect a low battery trigger crossing. A circuit for generating AZ and AZN from clock fc1 is shown in FIG. 9.

FIG. 8 shows a cycle of operation of the low battery detector circuit 16, including its interaction with the power electronics circuit block 14.

An autozero occurs when the battery voltage Vbatt is higher than the detection trigger level Vtrig. Some time later, Vbatt drops below Vtrig, resulting in ALARMN going low which results in the power electronics being disabled, shown for illustration by turning off switch SP1. The battery voltage Vbatt later recovers, but ALARMN remains low. It will remain low until RESLBD is strobed low resetting the low battery detect latch.

It should be understood that, as stated above, various alternatives to the embodiment of the invention described herein may be employed in practicing the invention. It is intended that the following claims define the invention and that methods and structures within the scope of these claims and their equivalents be covered thereby.

What is claimed is:

1. Low voltage detection circuitry for detecting when a voltage signal Vbatt drops below a preselected trigger voltage Vtrig, the detection circuitry comprising:
    (a) a switched capacitor voltage divider that generates a ratioed voltage signal corresponding to changes in the voltage signal Vbatt;
    (b) comparator means for generating a changing output signal in response to changes in the ratioed voltage signal; and
    (c) means for generating a low voltage detect signal in response to a change in the comparator output signal when the ratioed voltage signal drops below the preselected trigger voltage Vtrig.

2. Low voltage detection circuitry for detecting when a voltage signal Vbatt drops below a preselected trigger voltage Vtrig, the detection circuitry comprising:
   (a) comparator means having inverting and non-inverting inputs whereby a positive changing signal applied to the inverting input results in a negative change at the comparator means output and a negative changing signal applied to the inverting input results in a positive change in the comparator means output;
   (b) means for applying a positive changing signal to the inverting input of the comparator means if the voltage signal Vbatt drops below the preselected trigger voltage Vtrig; and
   (c) means for generating a low voltage detect signal in response to a positive change in the comparator means output.

3. Low voltage detection circuitry for detecting when a voltage signal Vbatt drops below a preselected trigger voltage Vtrig, the detection circuitry comprising:
   (a) a switched capacitor voltage divider comprising
      (i) first and second capacitors having values CA1 and CA2, respectively, the upper plates of the first and second capacitors being commonly connected to an output node of the voltage divider;
      (ii) means for switching the lower plate of the first capacitor between ground and the voltage signal Vbatt;
      (iii) means for switching the lower plate of the second capacitor between a reference voltage Vref and ground whereby a positive voltage change occurs at the voltage divider output node if the voltage signal Vbatt is greater than (CA1/CA2) * Vref, and a negative voltage change occurs at the voltage divider output node if the voltage signal Vbatt is less than (CA1/CA2) * Vref, where (CA1/CA2) * Vref=Vtrig;
   (b) comparator means having inverting and non-inverting inputs whereby a positive voltage change applied to the inverting input results in a negative change at the comparator means output and a negative voltage change applied to the inverting input results in a positive change at the comparator means output, the inverting input being connected to the voltage divider output node, the non-inverting input being connected to the reference voltage Vref; and
   (c) means for generating a low voltage detect signal in response to a positive change in the comparator means output.

4. A method of detecting when a voltage level Vbatt drops below a preselected trigger voltage Vtrig, the method comprising:
   (a) switching the bottom plate of a first capacitor having a value CA1 between ground and the voltage level Vbatt;
   (b) switching the bottom plate of a second capacitor having value CA2 between a reference voltage Vref and ground, the top plates of the first and second capacitors being connected to a common node B, such that a positive voltage change occurs at node B if Vbatt is greater than (CA1/CA2) * Vref=Vtrig, and a negative voltage change occurs at node B if Vbatt is less than Vtrig;
   (c) sensing a negative voltage change at node B; and
   (d) generating a low voltage detect signal when a negative voltage signal is detected at node B.

5. A method as in claim 4 and including the additional step of disconnecting the voltage signal Vbatt from associated circuitry when a low voltage detect signal is generated.

6. A method of detecting when a voltage level Vbatt drops below a preselected trigger level Vtrig, the method comprising:
   (a) configuring an operational amplifier in unity gain, the non-inverting input of the operational amplifier being connected to the top plates of first and second precisely ratioed capacitors having values CA1 and CA2, respectively, the inverting input of the operational amplifier being connected to a reference voltage Vref;
   (b) charging the top plates of the first and second capacitors, and thus the non-inverting input of the operational amplifier, to Vref+Vos, where Vos is the offset voltage of the operational amplifier;
   (c) charging the bottom plates of the first and second capacitors to ground and Vref, respectively;
   (d) configuring the operational amplifier as a comparator;
   (e) switching the bottom plates of the first and second capacitors to Vbatt and ground, respectively, such that the charge on the top plates of the first and second capacitors is changed by dQ,
   where $dQ = Vbatt * CA2 - Vref * CA1$
   whereby if Vbatt is less than (CA1/CA2 * Vref), a negative change in voltage occurs at the non-inverting input of the operational amplifier causing the output of the operational amplifier to switch state; and
   (f) detecting that the operational amplifier has switched state.

* * * * *

UNITED STATES PATENT AND TRADEMARK OFFICE
CERTIFICATE OF CORRECTION

PATENT NO. : 4,952,864

DATED : August 28, 1990

INVENTOR(S): Pless et al.

It is certified that error appears in the above - identified patent and that said Letters Patent is hereby corrected as shown below:

Col. 1, line 28, "the3V" should be --the 3V--.

Col. 1, line 48, "sWitches" should be --switches--.

Col. 2, line 45, "ata" should be --at a--.

Col. 3, line 63, "improVe" should be --improve--.

Col. 3, line 65, "efined" should be --defined--.

Col. 5, line 18, "while" should be --where--.

Signed and Sealed this

Seventh Day of January, 1992

Attest:

HARRY F. MANBECK, JR.

*Attesting Officer*                *Commissioner of Patents and Trademarks*